United States Patent [19]

Kato et al.

[11] 4,070,986
[45] Jan. 31, 1978

[54] AUTOMATIC BLOOD SERUM APPLICATOR APPARATUS FOR CATAPHORETIC USE

[75] Inventors: Yutaka Kato, Tama; Teruo Ouchi, Hachioji; Kiyozo Koshiishi, Sagamihara, all of Japan

[73] Assignee: Olympus Optical Company, Ltd., Tokyo, Japan

[21] Appl. No.: 614,694

[22] Filed: Sept. 18, 1975

[30] Foreign Application Priority Data

Sept. 19, 1974   Japan .................... 49-108022

[51] Int. Cl.² .............................................. B05C 1/16
[52] U.S. Cl. ........................................ 118/7; 118/203; 118/243
[58] Field of Search ............... 118/243, 242, 263, 203, 118/104, 7, 9, 120, 425, 73, 401; 23/253 R, 230 B, 258.5

[56] References Cited

U.S. PATENT DOCUMENTS

| | | | |
|---|---|---|---|
| 1,433,976 | 10/1922 | Weightman et al. | 118/203 |
| 2,348,233 | 5/1944 | Turnock et al. | 118/243 X |
| 2,353,852 | 7/1944 | Rowland et al. | 118/242 X |
| 3,332,394 | 7/1967 | Cooke | 118/263 |
| 3,691,988 | 9/1972 | Clarke | 118/425 X |
| 3,903,908 | 9/1975 | Logue et al. | 118/425 X |

Primary Examiner—John P. McIntosh
Attorney, Agent, or Firm—Ostrolenk, Faber, Gerb & Soffen

[57] ABSTRACT

An apparatus for automatic application of blood serum to a serum bearing film for use in a cataphoretic process includes a serum supply station, a serum application station, a rinsing station and a drip station. The apparatus also comprises a guide along which a serum applicator is sequentially moved through each of these stations, as well as operation controlling microswitches and a cam assembly.

11 Claims, 9 Drawing Figures

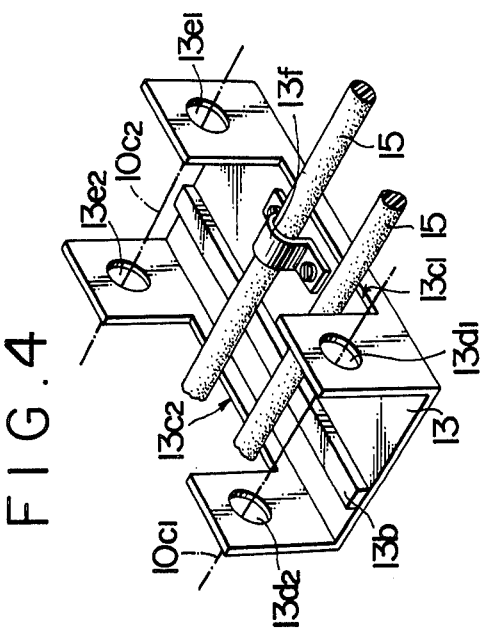

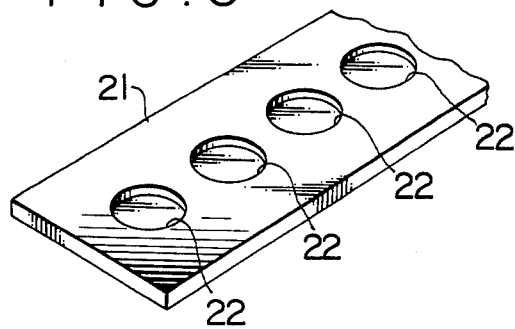
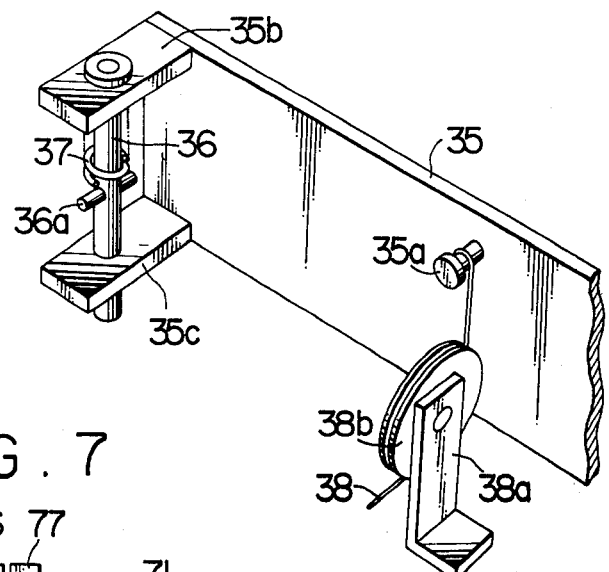
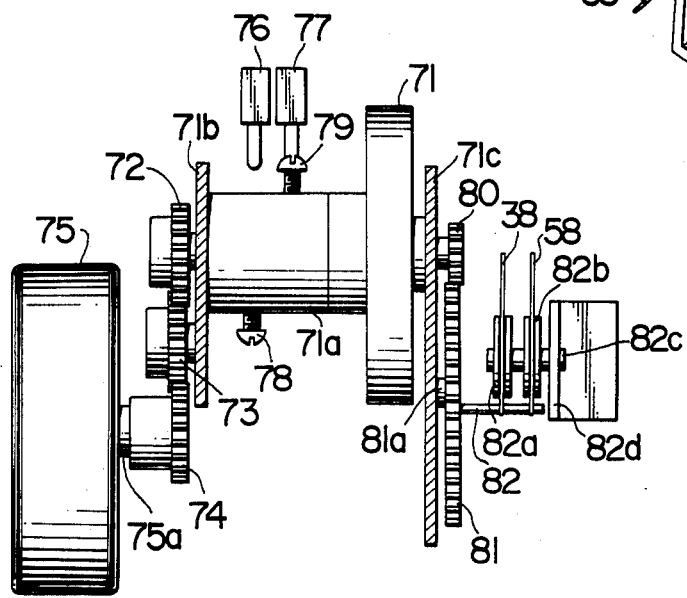

AUTOMATIC BLOOD SERUM APPLICATOR APPARATUS FOR CATAPHORETIC USE

BACKGROUND OF THE INVENTION

The invention relates to an apparatus for automatic application of blood serum to a serum bearing surface such as a sheet of cellulose acetate for use in the cataphoretic analysis.

The cataphoretic analysis of a blood serum is frequently employed in the diagnostic or medical examination. Specifically, a blood serum is applied to a bearing surface and electrically energized to provide fractionated patterns of serum components through the cataphoretic process. The fractionated patterns are then determined by a colorimetric technique. The operation of applying the blood serum in a cataphoretic analysis has been very inefficient because of the manual nature thereof in that the blood serum is drawn into a micropipette and then moved across a bearing film in the manner of drawing a line with a pen. In addition, the serum applying operation requires a high degree of skill, and is usually performed by a skilled operator with extreme care. Accurate determination is prevented if the application of the blood serum is not properly achieved.

It is therefore apparent that there has been a need for an apparatus which automatically performs the application of the blood serum. To meet such need, there has been proposed a serum applicator having an elongate arm which carries a plurality of vertically movable stems, to the free end of which are secured a penpoint-like member or a plurality of such members each having a thin groove in its tip end. The blood serum is supplied to the tip end of the respective members, which are then gently pressed against a bearing surface to apply the serum thereto in a simple manner.

Where such blood serum applicator is repeatedly used for a number of specimens, the individual members must be cleaned since otherwise any residue of previous serum remaining in the tip end of the members will become admixed with a next serum applied to thereby prevent an accurate cataphoretic action and hence an accurate quantitative determination. Thus, any residue on the penpoint of the members once used must be washed away as by rinsing in water. In addition, the rinsed members must be wiped by suitable means to remove any remaining moisture.

SUMMARY OF THE INVENTION

It is an object of the invention to provide a blood serum applicator apparatus capable of automatically performing the steps of supplying a blood serum, applying the blood serum to a bearing film which is being conveyed, rinsing applicator members which have once been used for application of the blood serum, and dripping moisture from the rinsed members.

With the apparatus according to the invention, the successive steps of supplying a blood serum, applying it, rinsing applicator members and dripping them are automatically performed in succession. Specifically, a fresh bearing film may be sequentially conveyed to a serum application station, and delivered to the next step such as a cataphoretic chamber subsequent to the application of the blood serum thereto, thus substantially improving the efficiency of the serum applying operation by removing a manual operation which has been employed heretofore. A uniform application of blood serum is assured by eliminating a variation from operator to operator of the application results. The apparatus can be advantageously utilized in an automated cataphoretic system.

BRIEF DESCRIPTION OF THE DRAWINGS

FIG. 2 is a front view of an exemplary serum applicator used in the apparatus of the invention;

FIG. 3 is a plan view of a guide used in the apparatus of the invention;

FIG. 4 is a perspective view of one example of a carriage;

FIG. 5 is a perspective view of a serum receiving dish;

FIG. 6 is a perspective view of a holder;

FIG. 7 is a plan view of a cam assembly;

DETAILED DESCRIPTION OF PREFERRED EMBODIMENTS

Figure 1:
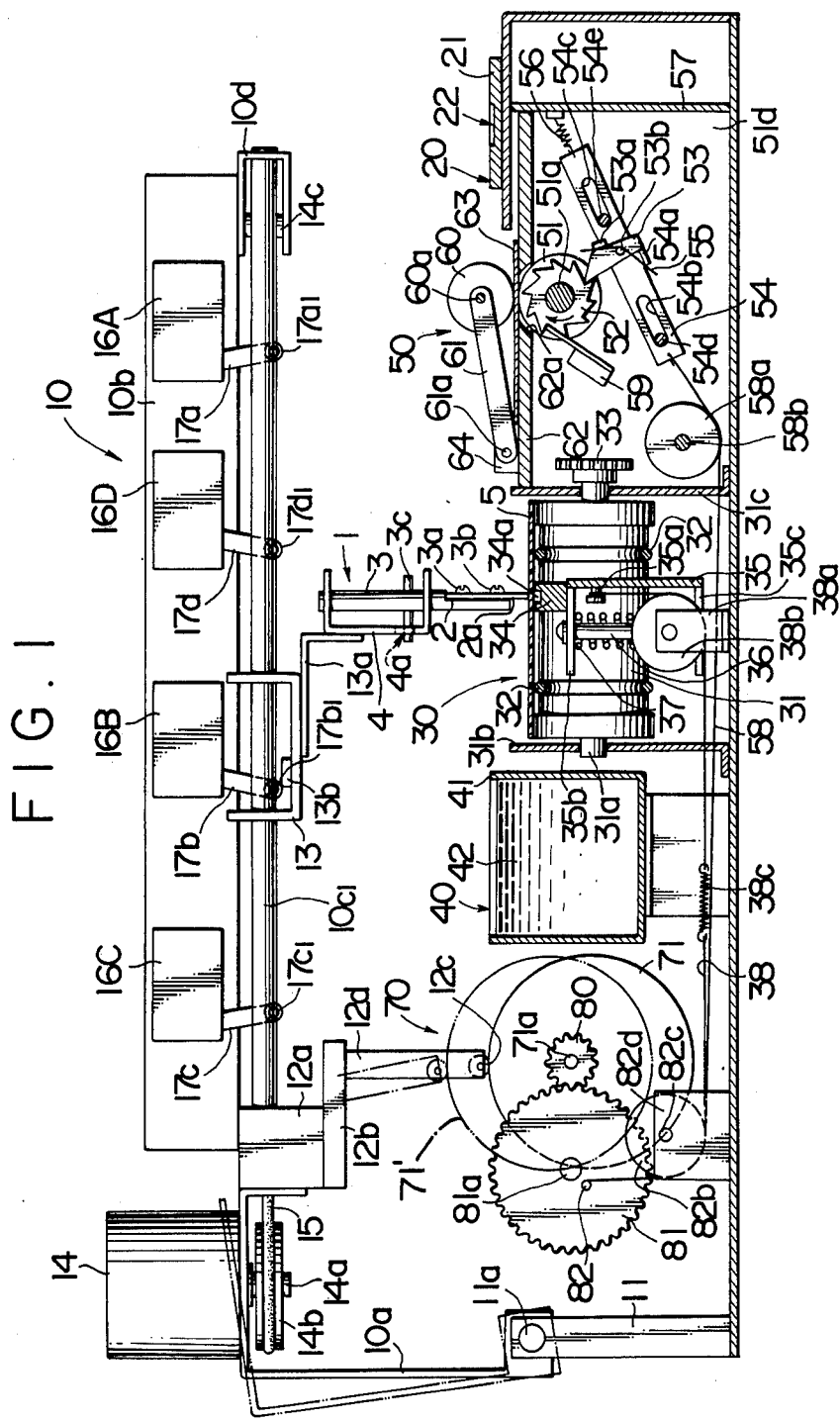
FIG. 1 is a side elevation, partly broken away, of the automatic blood serum applicator apparatus for cataphoretic use which is constructed in accordance with one embodiment of the invention.

Referring to FIG. 1, there is shown the apparatus for automatic application of the blood serum constructed according to the invention. Generally, the apparatus comprises a guide 10 along which a serum applicator 1 is moved to the right or left as viewed in this Figure; a serum supply station 20 where the serum is supplied to the applicator; a serum application station 30 where the serum is applied from the applicator to a serum bearing film 5, a rinsing station 40 where the applicator is rinsed, a drip station 50 where the applicator is dripped, and a cam assembly 70 which moves the guide 10 in the vertical direction.

Construction of the applicator 1 is fully shown in FIG. 2 wherein it will be noted that the applicator 1 comprises a plurality of penpoint-like members 2 having a narrow groove in its forward end 2a and secured to stems 3 by set screws 3a, 3b, the stems being mounted on a support arm 4. A serum is applied to the forward end 2a of the respective member 2, which is then lightly urged against the film 5 for application thereto. Pins 3c fixedly mounted on the stems 3 engage vertically elongated slots 4a formed in the support arm 4 for vertical movement thereof.

Returning to FIG. 1, a post 11 is shown at the left-hand side of this Figure and has a pivot 11a on which a downwardly extending base end 10a of the guide 10 is pivotally mounted. A mounting plate 12a is fixedly attached to the guide 10 at a position to the right of the base end 10a, and in turn fixedly carries another mounting plate 12b, to which the top end of a vertically extending arm member 12d is secured, the arm member having a roller 12c pivotally mounted thereon. Fixedly connected with the mounting plate 12a are the left-hand end of a longitudinal support plate 10b as well as the left-hand end of a pair of parallel rails 10c1, 10c2 (see FIG. 3), the right-hand end of the rails 10c1, 10c2 being carried by a mounting plate 10d which is secured to the right-hand end of the support plate 10b (see FIG. 3). A carriage 13 is slidably mounted on the pair of rails 10c1, 10c2 by passing these rails through two pairs of aligned apertures 13d1, 13d2 and 13e1, 13e2 formed in the carriage 13 (see FIG. 4), and the serum applicator 1 is fixedly attached to the underside of the carriage 13 by means of a mounting member 13a.

As indicated in FIG. 1, a motor 14 is fixedly mounted on the base plate 10a, and has a shaft 14a on which a pulley 14b is mounted. The mounting plate 10d carries a pivot 14c on which a pulley 14d is mounted (see FIG. 3), and an endless belt 15 extends around the pulleys 14b, 14d (see FIG. 3). In the region of the endless belt 15, the carriage 13 is formed with a pair of notches 13c1, 13c2 (FIG. 4), through which the endless belt 15 extends. The bottom of the carriage 13 is fixed to one run of the belt 15 by means of a clamping member 13f. It is to be noted that the bottom of the carriage 13 is also provided with a switch operating member 13b which is adapted to selectively operate microswitches 16A, 16B, 16C and 16D which are in turn fixedly mounted on the support plate 10b in the region of the serum supply station 20, the serum application station 30 and the like. These microswitches are associated with respective actuators 17a, 17b, 17c or 17d which are adapted to be operated only when they are urged in one direction, that is, to the left, as viewed in FIG. 1. The actuators 17a, 17b, 17c and 17d are provided with contacts 17a1, 17b1, 17c1 and 17d1, respectively, which are sequentially abutted by the switch operating member 13b of the carriage 13.

The carriage 13 is moved when driven by the motor 14 through the belt 15, but as the operating member 13b of the carriage 13 moves to the position of the respective microswitches 16A, 16B, 16C or 16D, the operating member abuts against one of the actuators, for example 17b as illustrated in FIG. 1, to operate the microswitch 16B to thereby deenergize the motor 14, thus stopping the carriage 13 at such position.

A dish 21 is disposed in the serum supply station 20, and includes a number of recesses 22 as shown in FIG. 5 which are equal in number to the number of the applicator members 2 and which receive the serum to be examined.

The serum application station 30 includes a pair of rollers 31 (one of which is not shown) which have their shafts 31a rotatably mounted in a pair of support plates 31b and 31c. The rollers divide the length through which the applicator 1 extends into substantially equal intervals. A plurality of conveying belts 32 are entrained around the rollers, and a gear 33 is coupled to the same shaft as the rollers 31 and is rotated by suitable means, not shown, for operating the rollers 31 and belt 32 to convey the serum bearing film 5 in a direction perpendicular to the plane of the sheet containing FIG. 1. A retainer 34 in the form of an elongated bar having a length corresponding to that of the applicator 1 is formed with a longitudinally extending groove 34a in its top surface, and is secured to and supported by holder 35 (see FIG. 6) whose arms 35b, 35c are slidably mounted on a shaft 36 and which is normally urged upward by a spring 37 disposed around the shaft. The lower end of this spring 37 is received by a pin 36a secured to the shaft 36. A wire 38 has its one end secured to a bolt 35a which is fixedly mounted on the holder 35 at a suitable location, and extends around a pulley 38b which is rotatably mounted on a mount 38a. As will be described later, by pulling the wire 38 to the left, the holder 35 can be lowered against the resilience of the spring 37, thus also lowering the retainer 34.

The rinsing station 40 where the applicator members 2 are rinsed includes a vessel 41 containing a supply of rinsing water 42.

The drip station 50 (see FIG. 1) includes a paper filter feed roller 51 which has its shaft 51a supported by support plates 51b, and a ratchet wheel 52 is mounted on the shaft 51a. A pawl 53 is pivotally mounted on a support piece 54 at pivot 53b, and is urged for clockwise rotation by a spring 55 which has its opposite ends engaged with a projection 53a on the pawl 53 and a projection 54a on the support piece 54, respectively. However, the rotation of the pawl 53 is prevented by the engagement of its end against the projection 54a. The support piece 54 is formed therein with a pair of elongated slots 54b and 54c which are engaged by stationary pins 54d and 54e, respectively. A spring 56 has its one end secured to one end of the support piece 54 while its other end is anchored to a partition 57. A wire 58 has its one end secured to the other end of the support piece 54, and extends around a pulley 58a which is rotatably mounted on a stationary shaft 58b. It will be appreciated that the wire can be operated to cause movement of the support piece 54 over an extent as permitted by the engagement between the slots 54b, 54c and the pins 54d, 54e, thus causing a movement of the pawl 53. As will be further described later, the wire 58 can be pulled to the left to disengage the pawl 53 from the ratchet wheel 52 so as to permit an incremental rotation of the latter corresponding to one tooth pitch thereof. This results in a corresponding incremental rotation of the roller 51. The ratchet wheel is also engaged by a detent piece 59 which prevents a reverse rotation thereof. A pair of rollers 60 (one of which is not shown) are disposed above the opposite ends of the roller 51, which extends slightly above the surface of a base 62 through a notch 62a formed therein so as to be in abutting relationship with the rollers 60. The rollers 60 have their axles 60a rotatably mounted on a pair of support rods 61. When a paper filter 63 is disposed on the surface of the base 62, it is held sandwiched between the roller 51 and the pair of rollers 60. As indicated in FIG. 1, one of the support rods, 61, which carries the roller 60 is made so as to be pivotal about an axle 61a supported by a mount 64 so that the roller 60 can be moved vertically, thereby facilitating the placement of the paper filter 63 on the surface of the base 62.

FIG. 7 shows a specific construction of the cam assembly 70 in plan view. The assembly includes an eccentric cam 71 having a rotary shaft 71a which is supported by a pair of support plates 71b, 71c and on which is fixedly mounted a gear 72, which is in turn operatively connected with the rotary shaft 75a of a motor 75 through a pair of transmission gears 73 and 74. A pair of microswitches 76 and 77 are disposed so as to be operated by a pair of pins 78 and 79 which are fixedly mounted on the rotary shaft 71a of the eccentric cam 71. The microswitch 76 serves to interrupt the operation of the motor 75 and initiating the operation of the motor 14 while the microswitch 77 operates during a particular phase of movement of the serum applicator 1 as will be described later to interrupt the operation of the motor 75 for a while, which is again set in motion at a given period of time determined by a timer. During such period of time, both motors 14 and 75 remain at rest. The assembly also includes a gear 80 fixedly mounted on the shaft 71a of the cam 71 and which meshes with a reduction gear 81 mounted on a shaft 81a, the gear ratio of these gears being 1:4. The gear 81 has a pin 82 fixedly mounted thereon at a position spaced from the axis thereof, and the wires 38 and 58 which serve to operate the retainer 34 and the feed roller 51 are connected with the pin 82 through the interposition of a pair of coaxial pulleys 82a, 82b of an equal diameter and mounted on a common shaft 82c which is in turn supported by a support plate 82d. It will be understood that the rotation of the eccentric cam 71 results in a revolution of the pin 82 about the axis 81a, thereby loosening or tensioning the wires 38, 58 for vertically moving the retainer 34 or feeding the paper filter 63. It will be noted from FIG. 1 that a buffering spring 38c is connected intermediate the length of the wire 38.

Figure 8:
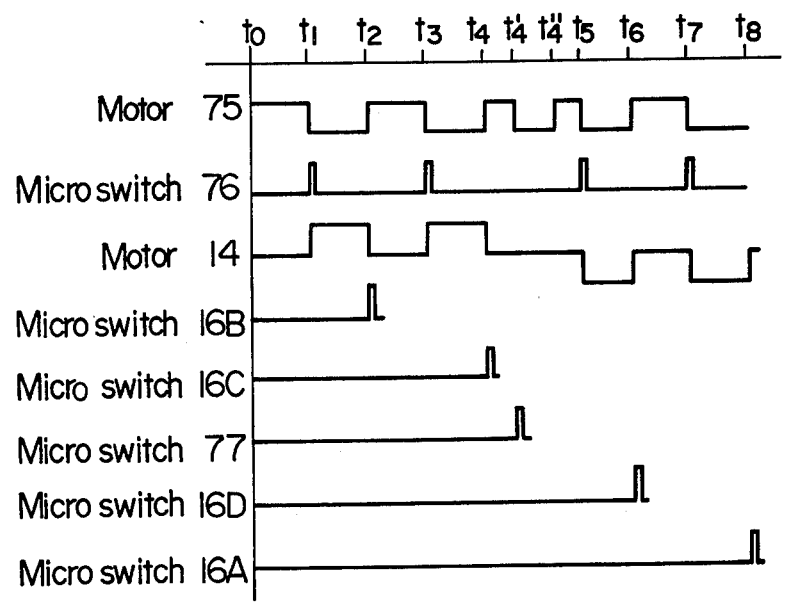
FIG. 8 graphically illustrates a series of timing diagrams, showing the timing of the operation of various microswitches and motors.

The overall operation of the apparatus according to the invention will now be described with reference to the timing charts of FIG. 8 which show the relationship between the operations of the various motors and microswitches. The operation starts with the penpoint-like members 2 of the serum applicator located directly above the serum dish 21. In FIG. 8, the motor 75 begins rotation at $t_0$, whereby the gear 72 is rotated through the gears 74, 73 to rotate the eccentric cam 71 in turn, as shown in FIG. 7. The rotation of the eccentric cam 71 causes it to be displaced gradually from the position 71', shown in phantom lines to the solid line position, shown in FIG. 1, so that the arm member 12d which bears against the cam surface with the roller 12c carried thereon descends, with a consequent descent of the guide 10 until the solid line position is reached, whereupon each tip end 2a of the individual penpoint-like members 2 of the serum applicator 1 is inserted into respective blood serums to be determined which are contained in the recesses 22 of the serum dish 31. As the eccentric cam 71 further rotates, the arm member 12d begins to rise again, and assumes the position shown in phantom lines in FIG. 8 at $t_1$. By positioning the pin 78 mounted on the shaft 71a of the eccentric cam 71 so that it operates on the microswitch 76 at such time, the microswitch 76 interrupts the rotation of the motor 75, whereby the eccentric cam 71 ceases to rotate. At the same time, the motor 14 is set in motion, whereby the endless belt 15 moves along the guide 10 together with the carriage 13. Consequently, the serum applicator 1 fixedly mounted on the carriage 13 moves to the left, as viewed in FIG. 1. When it reaches the microswitch 16B, the switch operating member 13b of the carriage 13 pushes up the contact of the microswitch 16B to operate it. Before reaching the microswitch 16B, the carriage 13 passes by the position of the microswitch 16D, which is however not operated since it is only operated by a movement to the right, as viewed in FIG. 1, of the carriage 13. As indicated at $t_2$ in FIG. 8, the actuated microswitch 16B interrupts the rotation of the motor 14 and re-initiates the rotation of the motor 75. This causes a vertical movement of the guide 10 and hence of the serum applicator 1 by a similar operation as mentioned previously. When the serum applicator 1 descends, the pin 82 on the reduction gear 81 moves in a direction to reduce the tension in the wire 31 which serves to pull the holder 35, and the pulling force of the wire 38 which is effective on the holder 35 is at its minimum in the lowermost position of the serum applicator 1 or in the position of the pin 82 which is shown in FIG. 1, so that the holder 35 is biased upward by the spring 37, thus moving the retainer 34 to a position in which it bears against the lower surface of the bearing film 5. In this manner, as the applicator 1 descends, the tip end 2a of the individual penpoint-like members 2 contacts and presses the bearing film 5 against the retainer 34 with a slight pressure, enabling a satisfactory application of the serum. As the eccentric cam 71 further rotates, the arm member 12d is raised, and the serum applicator 1 is also raised together with the guide 10. The reduction gear 81 also rotates as the eccentric cam 71 rotates, so that the pin 82 thereon pulls the wire 38, whereby the retainer 34 begins its downward movement together with the holder 35. When the retainer 34 has moved downward a sufficient distance to be completely clear from the lower surface of the bearing film 5, the roller 31 is driven to run the conveyer belt 32, whereby the bearing film 5 carrying the blood serum applied is conveyed to the next process step.

At $t_3$ shown in FIG. 8, or when the guide 10 reaches its uppermost position, the microswitch 76 is activated to stop the motor 75 and to energize the motor 14, whereby the carriage 13 is moved to the left along the guide 10. When the carriage 13 reaches the position of the microswitch 16C, or at $t_4$ of FIG. 8, the microswitch 16C is activated to stop the motor 14 and to energize the motor 75 again, thus causing the guide 10 to descend as mentioned previously. The position of the microswitch 16C is established so that the penpoint-like members 2 of the serum applicator 1 are immersed into the washing vessel 41 at this time. In the lowermost position of the guide 10 and the serum applicator 1, the pin 79 activates the microswitch 77 ($t'_4$ shown in FIG. 8) to stop the motor 75, thereby maintaining the member 2 immersed in the washing solution 42. The immersion of the member 2 is maintained for a length of time which is sufficient to ensure that the serum which remains on the members 2 are completely removed by the washing water 42. Subsequently, at $t''_4$ shown in FIG. 8, the timer is activated to set the motor 75 in motion, whereby the guide 10 is raised.

At $t_5$ in FIG. 8, the microswitch 76 is activated to stop the motor 75 and to reverse the motor 14, whereby the carriage 13 is moved in the opposite direction or to the right. For the reason mentioned previously, the microswitches such as 16C are not operated during such movement, and when the carriage 13 reaches the position of the microswitch 16D (at $t_5$), the motor 14 is deenergized and the motor 75 is set in motion again, repeating a similar operation. The downward movement of the guide 10 causes the members 2 of the serum applicator 1 to be pressed against the paper filter 63, removing the rinsing water used during the washing step from these members. After removal of the rinsing water, the upward movement of the guide activates the microswitch 76 again at $t_7$ to stop the motor 75 and to energize the motor 14 in the reverse direction, and the carriage 13 moves to the right until the position of the microswitch 16A is reached, whereupon this switch stops the motor 14 at $t_8$ shown in FIG. 8. This completes one cycle of operation.

During one cycle of operation, the eccentric cam 71 undergoes four revolutions while the reduction gear 81 undergoes one revolution. Since the pin 82 on the reduction gear 81 is located so that the wire 38 is in its loosest condition to permit the retainer 34 to be raised, as shown in FIG. 1, when the serum is applied by the applicator 1 to the bearing film 5. On the other hand, the other wire 58 is tensioned once during one revolution of the reduction gear 81 or during one cycle of operation of the apparatus according to the invention. The wire 58 causes a movement of the support piece 54, causing the pawl 53 mounted thereon to rotate the ratchet wheel 52 through an increment corresponding to one tooth pitch. This rotates the roller 51, feeding the paper filter 63 by a given length. Thus, the paper filter 63 which becomes wetted after removing the rinsing water from the members 2 is moved out of the dripping station by the next time the members 2 are pressed thereagainst, thus presenting a fresh length thereof. Merely pressing the tip end 2a of the members 2 against the paper filter 63 during the time the serum applicator 1 moves vertically does not provide a satisfactory dripping operation, and it is desirable to maintain the members 2 pressed against the paper filter 63 for a certain duration in order to assure a complete removal of the rinsing water from the members 2. At this end, the microswitch 77 may be activated during the dripping step, so that its combination with a timer (not shown) which is preset to a given time length deenergizes the motor 75 for a given time when the serum applicator 1 is in its lower position and to re-energize it when the preset time length has lapsed.

Figure 9:
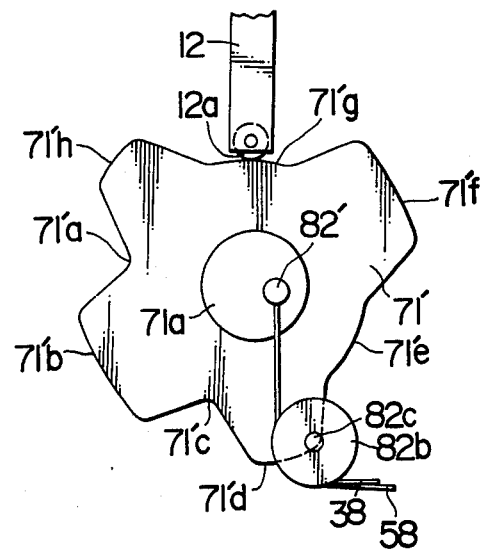
FIG. 9 is a front view of another example of the cam assembly.

FIG. 9 shows another example of the cam assembly 70 which includes a profiled cam 71' in place of the eccentric cam 71. The cam 71' includes a plurality of recesses 71'a, 71'c, 71'e and 71'g which lie on a common circumference of a reduced diameter than that of another circumference on which a plurality of cam lobes 71'b, 71'd, 71'f and 71'h lie. When the arm 12 bears against one of the cam recesses, the guide 10 is in its lower position, while the guide 10 is in its upper position when the arm 12 bears against one of the cam lobes. With this cam assembly, no reduction gear is used, and instead the wires 38 and 58 are directly connected with a pin 82' on the cam 71'. In other respects, the described cam assembly is similar to the previous one.

The operation of the apparatus incorporating the cam assembly which includes the cam 71' will be described briefly. The operation starts with the abutting engagement of the arm 12 against the cam lobe 71'h, which corresponds to the position of the carriage 13 in which it activates the microswitch 16A or to the location of the applicator 1 in the serum supply station 20. As the motor 75 rotates to rotate the cam 71', the arm 12 bears against the cam recess 71'a, whereby the arm 12 descends together with the guide 10 and the applicator 1 for providing a supply of the serum to the applicator. As the cam 71' further rotates to cause the arm 12 to bear against the cam lobe 71'b, the applicator 1 is raised. By suitably locating pins 78 for operating the microswitch 76 in the various steps so as to control the rotation of the motor 14, the carriage 13 is moved along the guide together with the applicator 1. The operation of the microswitches, such as that of the microswitch 16B to stop the carriage 13, is completely similar to the operation previously described. In this manner, all of the steps beginning with the supply of the serum until the dripping can be repeatedly performed in a sequential manner. It will be noted that the length of the cam recesses 71'a, 71'c, 71'e and 71'g can be determined so as to provide the necessary operation time in the various steps while the length of the cam lobes 71'b, 71'd, 71'f and 71'h can be adjusted to the required time of movement of the applicator 1 between adjacent steps.

When one cycle of operation is completed by one revolution of the cam 71', the wire 58 is pulled through a given distance to feed the paper filter 63 by a given distance to thereby present a fresh portion thereof at the dripping position for the applicator 1 in the same manner as mentioned previously. It is to be noted that the serum bearing film 5 is subjected to a pretreatment by a buffer solution applicator device to be described below prior to the application of the serum thereto by the serum applicator 1.

What is claimed is:

1. A blood serum applicator apparatus for cataphoretic use comprising:
    a serum applicator;
    a blood serum supply station and means for supplying blood at said supply station;
    a blood serum application station;
    a rinsing station at which said serum applicator is subjected to a rinsing fluid; means supplying rinsing fluid located at said rinsing station;
    a dripping station including means for removing said rinsing fluid from said serum applicator;
    a guide along which said serum applicator is moved to be sequentially passed through each of said stations;
    a plurality of microswitches located at spaced intervals on said guide, each said microswitch for stopping the movement of said serum applicator when said serum applicator has reached a different one of said stations;
    a cam assembly for causing a generally vertically downward and upward movement of said serum applicator when its movement is stopped by activation of one of said microswitches located on said guide; and
    a station advancing control microswitch means mounted on said cam assembly, said control microswitch means being effective to cause movement of said serum applicator along said guide from one of said stations to the next, thus automatically achieving respective operations required for the application of the serum in succession.

2. The apparatus of claim 1 wherein said cam assembly comprises a profiled cam having a plurality of lobes whose shape and size determine the frequency and duration of said vertically downward and upward movements of said serum applicator.

3. The apparatus of claim 2 wherein said cam assembly further comprises a cam follower having a first and a second end, said first end being connected to said guide, said second end adapted to follow the profile of said profiled cam.

4. A blood serum applicator apparatus for cataphoretic use comprising:
    a serum applicator;
    a blood serum supply station and means for supplying blood at said supply station;
    a blood serum application station;
    a rinsing station at which said serum applicator is subjected to a rinsing fluid; means supplying rinsing fluid located at said rinsing station;
    a dripping station including means for removing said rinsing fluid from said serum applicator;
    said means for removing said rinsing fluid from said serum applicator comprises an absorptive medium which is contacted by said applicator when said applicator is located at said dripping station;
    a guide along which said serum applicator is moved to be sequentially passed through each of said stations;
    a plurality of microswitches located at spaced intervals on said guide, each said microswitch for stopping the movement of said serum applicator when said serum applicator has reached a different one of said stations;

a cam assembly for causing a generally vertically downward and upward movement of said serum applicator when its movement is stopped by activation of one of said microswitches located on said guide; and a station advancing control microswitch means mounted on said cam assembly, said control microswitch means being effective to cause movement of said serum applicator along said guide from one of said stations to the next, thus automatically achieving respective operations required for the application of the serum in succession.

5. The apparatus of claim 4, wherein said means for removing said rinsing fluid from said serum applicator further comprises means for causing said applicator to contact a different portion of said absorptive medium each time said applicator brought into contact with said absorptive medium.

6. The apparatus of claim 5, wherein said means for causing said applicator to contact a different portion of said absorptive medium comprises means for moving said absorptive medium to a new position after said applicator contacts said absorptive medium.

7. The apparatus of claim 6, wherein said means for moving said absorptive medium comprises:

a feed roller in operative contact with said absorptive medium;

means for rotating said feed roller a predetermined distance after said applicator contacts said absorptive medium.

8. The apparatus of claim 7, wherein said means for rotating the feed roller comprises:

a ratchet and pawl assembly adapted to rotate said feed roller said predetermined distance each time said pawl is moved from a first to a second position;

means for moving said pawl from said first to said second position after said applicator contacts said absorptive medium.

9. The apparatus of claim 8, wherein said means for moving said pawl comprises:

spring means urging said pawl into said first position;

means associated with said cam assembly for urging said pawl into said second position after said applicator contacts said absorptive medium, said means including a wire connected between said pawl and a pin whose position is controlled by the rotation of said cam assembly.

10. A blood serum applicator apparatus for cataphoretic use comprising:

a serum applicator;

a blood serum supply station and means for supplying blood at said supply station;

a blood serum application station;

a rinsing station at which said serum applicator is subjected to a rinsing fluid; means supplying rinsing fluid located at said rinsing station;

a dripping station including means for removing said rinsing fluid from said serum applicator;

a guide along which said serum applicator is moved to be sequentially passed through each of said stations;

a plurality of microswitches located at spaced intervals on said guide for stopping the movement of said serum applicator when said serum applicator has reached each one of said stations;

a cam assembly for causing a vertically downward and upward movement of said serum applicator when its movement is stopped by activation of one of said microswitches located on said guide;

an absorptive medium which is contacted by said applicator when said applicator is located at said dripping station thereby removing said rinsing fluid from said serum applicator;

means for moving said absorptive medium to a new position after said applicator contacts said absorptive medium such that said applicator contacts a different portion of said absorptive medium each time said applicator is brought into contact with said absorptive medium; and a station advancing control microswitch mounted on said cam assembly, said control microswitch being effective to cause movement of said serum applicator along said guide from one of said stations to the next, thus automatically achieving respective operations required for the application of said serum in succession.

11. The apparatus of claim 10 wherein said cam assembly comprises a profiled cam having a plurality of lobes whose shape and size determine the frequency and duration of said vertically downward and upward movements of said serum applicator.

* * * * *